United States Patent [19]
Legg et al.

[11] Patent Number: 5,511,549
[45] Date of Patent: Apr. 30, 1996

[54] NORMALIZING AND CALIBRATING THERAPEUTIC RADIATION DELIVERY SYSTEMS

[75] Inventors: David B. Legg, Corona; George Coutrakon; Jon W. Slater, both of Redlands; Daniel W. Miller, Yucaipa; Michael F. Moyers, Redlands; Jeffrey V. Siebers, Grand Terrace, all of Calif.

[73] Assignee: Loma Linda Medical Center, Loma Linda, Calif.

[21] Appl. No.: 404,207

[22] Filed: Feb. 13, 1995

[51] Int. Cl.$^6$ ........................................................ A61B 6/00
[52] U.S. Cl. ...................... 128/653.1; 128/659; 250/252.1
[58] Field of Search ............................ 250/370.07, 252.1, 250/251, 307; 128/653.1, 659

[56] References Cited

U.S. PATENT DOCUMENTS

| | | |
|---|---|---|
| 3,777,124 | 12/1973 | Pavkovich . |
| 4,190,772 | 2/1980 | Dinwiddie et al. . |
| 4,497,061 | 1/1985 | Hounsfield . |
| 4,789,930 | 12/1988 | Sones et al. . |
| 4,870,287 | 9/1989 | Cole et al. . |
| 5,027,818 | 7/1991 | Bova et al. . |
| 5,117,829 | 6/1992 | Miller et al. . |

OTHER PUBLICATIONS

Slater, James M. et al., "The Proton Treatment Center at Loma Linda University Medical Center: Rationale for and Description of its Development", *I.J. Radiation Oncology Biol. Phys.* vol. 22, pp. 383–389, 1992.

Coutrakon, G. et al., "A Prototype Beam Delivery System for the Proton Medical Accelerator at Loma Linda", *Medical Physics*, vol. 18, No. 6, Nov./Dec. 1991.

Wong, C. K. et al., "Calibration procedure in dual–energy scanning using the basis function technique", *Medical Physics*, vol. 10, No. 5, Sep./Oct. 1993, pp. 628–635.

Siebers, J. V. et al., "Routine Quality Assurance for a Proton Radiation Therapy Facility", Proton Therapy Cooperative Group Spring 1992 Meeting.

*Primary Examiner*—Krista M. Zele
*Assistant Examiner*—Shawna J. Felger
*Attorney, Agent, or Firm*—Knobbe, Martens, Olson & Bear

[57] ABSTRACT

The present invention is directed to a method for radiation beam therapy delivery system normalization and dose calibration. A prescribed treatment plan is compared to a database of pre-existing and pre-calibrated treatment plans. Upon existence of a matching plan, appropriate calibration factors are assigned to the delivery system monitors according to the pre-existing plan. Variations in delivery system operation are corrected by independent correction of all delivery system monitors established by standard relative calibration taken prior to patient treatment. The advantages of the present invention are particularly significant for proton therapy facilities containing a plurality of delivery systems. The method permits a prescribed treatment to be administered with accuracy not only at the station associated with the initial treatment planning, but at any available delivery station.

7 Claims, 7 Drawing Sheets

NORMALIZING AND CALIBRATING THERAPEUTIC RADIATION DELIVERY SYSTEMS

FIELD OF THE INVENTION

The present invention relates to calibration techniques in radiation therapy, particularly proton beam therapy. Specifically the invention pertains to proton beam delivery system normalization and dose calibration.

BACKGROUND OF THE INVENTION

Determining optimum conditions for accurate and precise dosimetry continues to be a major concern in radiation therapy. Indeed in all methods of radiation treatment it is imperative to choose operating conditions which provide effective radiation delivery to an afflicted tissue volume, while minimizing the impact on healthy outlying tissue. Conventional radiation therapy utilizes electron beams, x-rays or gamma rays as ionizing radiation applied to malignant tissue. To this end, accurate, repeatable delivery systems and calibration procedures have been developed, whereupon once an appropriate treatment plan is established, the plan may in principle be administered at any equivalent delivery system without modification or recalibration. In this respect, conventional radiation therapy may be regarded much like any other administered medication where techniques and standards have established a high degree of accuracy and precision. However, unlike many other forms of medication, radiation can be administered only at the time of its creation.

Photons such as X-rays or γ-rays generally deposit a radiation dose in an exponentially attenuated manner with tissue penetration depth, thus disturbing much tissue before reaching a desired target volume. High energy proton beams on the other hand present several distinct advantages residing principally in their physical characteristics. Protons carry more momenta for a given beam energy, creating a highly forward directed beam upon tissue traversal. Due to their mass and charge, the rate of energy loss from a proton beam rises as the beam loses energy, reaching a maximum near the stopping point or so-called Bragg peak. Thus in comparison to other forms of radiation, proton beams offer the possibility of delivering more effective therapeutic doses directed principally within well-defined target volumes. These conditions also mean that proton delivery systems should be at least as accurate and precise as their conventional counterparts.

In order to exploit these advantages, technology must be developed to facilitate clinically useful proton beams; specifically, accurate and precise dose delivery over time, and component exchange. In most proton therapy systems around the world, the proton accelerators were originally built for physics research and later adapted for part-time clinical research and therapy. One of the basic components of a proton therapy facility is a beam delivery system capable of delivering precise dose distributions to the target volume within a patient. To this end, a beam delivery system may comprise, for example, a beam spreading device to produce a large, uniform field, a range modulator to disperse the Bragg peak and various beam detectors to measure fluence, centering and dose distribution. A more detailed description of beam delivery system components and their function is provided in an article by Coutrakon et al., "A Prototype Beam Delivery System for the Proton Medical Accelerator at Loma Linda," Medical Physics, vol. 18, no. 6, 1093–1099 (1991).

To understand and predict dose delivery, a suitable dynamic model of proton transport and energy deposition could be developed, specific to the type of delivery system and capable of establishing dosimetric capability in a deterministic manner. Unfortunately however, previous attempts to model dose-distribution have not succeeded in reaching the level of accuracy established by accepted medical practice. As is commonly done, a calibration is performed for every treatment plan to be administered. To ensure accurate dosimetry for a prescribed treatment plan, delivery system radiation monitors are precalibrated with an absolute standard under the conditions of treatment. The method of individual treatment plan calibration remains the standard practice.

The imminent advantages of proton beam therapy can be realized only with the development of dedicated, clinically based facilities. One such therapy facility, located at the Loma Linda University Medical Center, was purposely built to provide therapeutic proton beams to a multiplicity of treatment rooms. An overview of the facility and its development is provided in "The Proton Treatment Center at Loma Linda University Medical Center: Rationale for and Description of its Development," J. M. Slater et al., Intl. J. Radiation Oncology, vol. 22, no. 2, 1992, pp. 383–389. Having one proton synchrotron source, the proton beam itself can be delivered to only one treatment station at time. Treatment calibration, however, is a time consuming operation and represents the majority of operating time of an expensive proton beam facility. As such, a lengthy calibration period for each treatment plan severely limits the efficiency and potential cost reduction offered by a clinically-based, multiple treatment center facility. Hence, while the method of individual treatment plan calibration may be acceptable for an experimental or developmental proton beam facility, it is clearly insufficient for the operation of a clinically based proton beam therapy facility.

SUMMARY OF THE INVENTION

Proton beams represent a uniquely valuable contribution to radiation therapy. It is an object of the present invention to provide an improved technique for proton radiation dosimetry, allowing more efficient, cost effective use of proton radiation facilities.

In accordance with one aspect of the present invention, a method of treating a patient with proton radiation comprises an initial baseline calibration procedure of emitting a proton radiation beam having a standard beam configuration and detecting the resulting radiation dose. The specific patient treatment plan is calibrated by emitting a proton radiation beam having a beam configuration tailored for the specific treatment plan and sensing the radiation delivery. This detected signal is compared to a calibrated dose determination in accordance with the specific patient treatment plan to develop at least one treatment plan calibration factor. The radiation treatment is administered using the calibrated proton radiation beam configured for the specific treatment plan. Before a specific treatment plan is re-administered, another standard proton radiation beam is emitted and the resulting dose is detected. The standard configuration doses measured in both of the standard calibration procedures are compared to determine at least one normalizing factor for correcting subsequent radiation treatment calibration factors. Upon subsequent radiation treatment using a specific treatment plan beam configuration, the previously determined calibration factor is modified by the normalizing factor to maintain dosimetric accuracy. Thus, a patient is treated according to a specific treatment plan using the normalized treatment plan calibration factor. When a treatment plan is initially administered at a proton radiation beam delivery system, the preferred method of patient treatment allows the same treatment plan to be administered at a later time or at another radiation delivery system without the need for a new treatment plan calibration.

In a preferred embodiment of the method for treating patients with proton radiation, the normalizing and calibration factors corresponding to specific administered treatment plans and are stored in a database for comparison to future prescribed treatment plans. In the event of a matching treatment plan, normalizing and calibration factors stored in the database are called up for use to normalize and calibrate the current proton beam delivery means, thus eliminating a time-consuming patient calibration procedure.

In accordance with another aspect of the present invention, a proton radiation beam delivery apparatus for treating a patient with calibrated radiation doses comprises a means for receiving a proton radiation beam and directing thereby to a target position for depositing proton radiation. At least one proton radiation detector is associated with the aforementioned proton beam directing means, having an output representative of the proton radiation dose. The proton radiation beam delivery apparatus further comprises at least one radiation dose detector which is positioned to be movable between a first position at the radiation beam target position and a second position outside the radiation beam. The movable radiation dose detector is preferably used to measure the resulting dose from controlled radiation exposure. These data are used to calibrate and normalize the proton radiation detector associated with the radiation beam directing means.

DETAILED DESCRIPTION OF THE PREFERRED EMBODIMENTS

Figure 1:
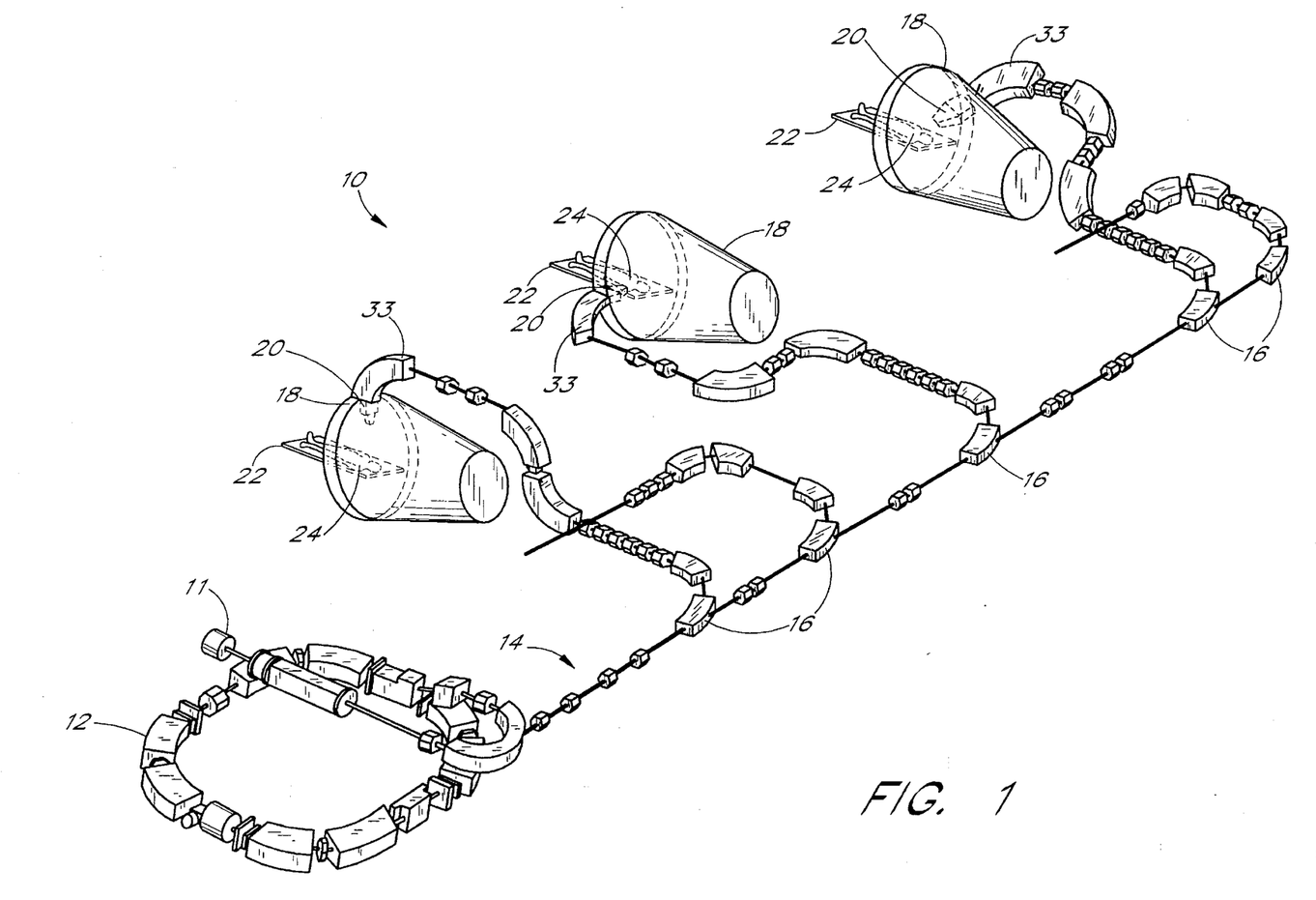
FIG. 1 is a schematic perspective view of a proton beam therapy facility for which the method of the present invention is particularly suited.

As shown in FIG. 1, a preferred form for a clinically-based charged particle beam therapy facility 10 begins with a charged particle source 11 and accelerator 12 connected to a beam transport and steering system 14. The source/accelerator 12 may, for example, comprise a proton synchrotron, while the transport system 14 may comprise a plurality of steering and focussing magnets with beam sensors distributed along an evacuated beam transport tube.

The beam transport system 14 connects to a series of swithchyards 16, comprised of an array of 45° dipole bending magnets which deflect the beam to any one of a plurality of beam focussing and deflection optics 33 leading to respective treatment locations having rotatable gantries 18. An exemplary proton beam treatment system is more fully disclosed in U.S. Pat. No. 4,870,287, herein incorporated by reference. Located within each gantry is a beam delivery system 20, which is configured to deliver therapeutic radiation doses to patient 22, according to a specific patient treatment plan.

In operation, charged particle beams of a predefined energy and fluence are generated by proton synchrotron 12 and transported by beam transport system 14 to switchyards 16. The switchyards 16 are configured to select a single gantry 18 for transport of radiation thereto. The rotatable gantry 18 is capable of orienting beam delivery system 20 with respect to patient 22, allowing directed deposition of radiation to a predefined location along the rotation axis or so-called isocenter 24. To facilitate accurate and precise dose delivery to patient 22, beam delivery system 20 is positioned, configured and calibrated for radiation delivery according to specifications of the patient treatment plan.

One of the central components of a proton therapy apparatus is the radiation delivery system 20, designed to deliver precise dose distributions to a target volume within a patient. In general, such delivery systems are comprised of components which may either modify or monitor specific properties of a radiation beam relevant to the treatment plan. The beam delivery system 20 may for example comprise a device to spread or otherwise modify the beam position and profile, a dispersive element to modify the beam energy and a plurality of beam sensors to monitor such properties. A more detailed description of beam delivery system components and function is provided in an article by Coutrakon et al., "A Prototype Beam Delivery System for the Proton Medical Accelerator at Loma Linda," Medical Physics, vol. 18, no. 6, 1093–1099 (1991), which is incorporated herein by reference. As depicted in the simplified partial plan view of FIG. 2, the exemplary beam delivery system 20 may comprise a nozzle housing 31 having a through beam path positioned coaxially with respect to incident beam 30. Disposed along the beampath of nozzle housing 31 are a plurality of beam modifying and sensing devices. Such modifying devices may for example comprise material scatterers 34, apertures 38 and 46, a range modulator 40, precollimator plates 44 and bolus 48. A coaxial X-ray generator 41 provides additional imaging capabilities for accuracy and precision in proton beam placement. Proton beam sensing devices typical for a radiation beam delivery system may comprise a Secondary Emission Monitor (SEM) 32 and ionization chambers 36 and 42.

Figure 2:
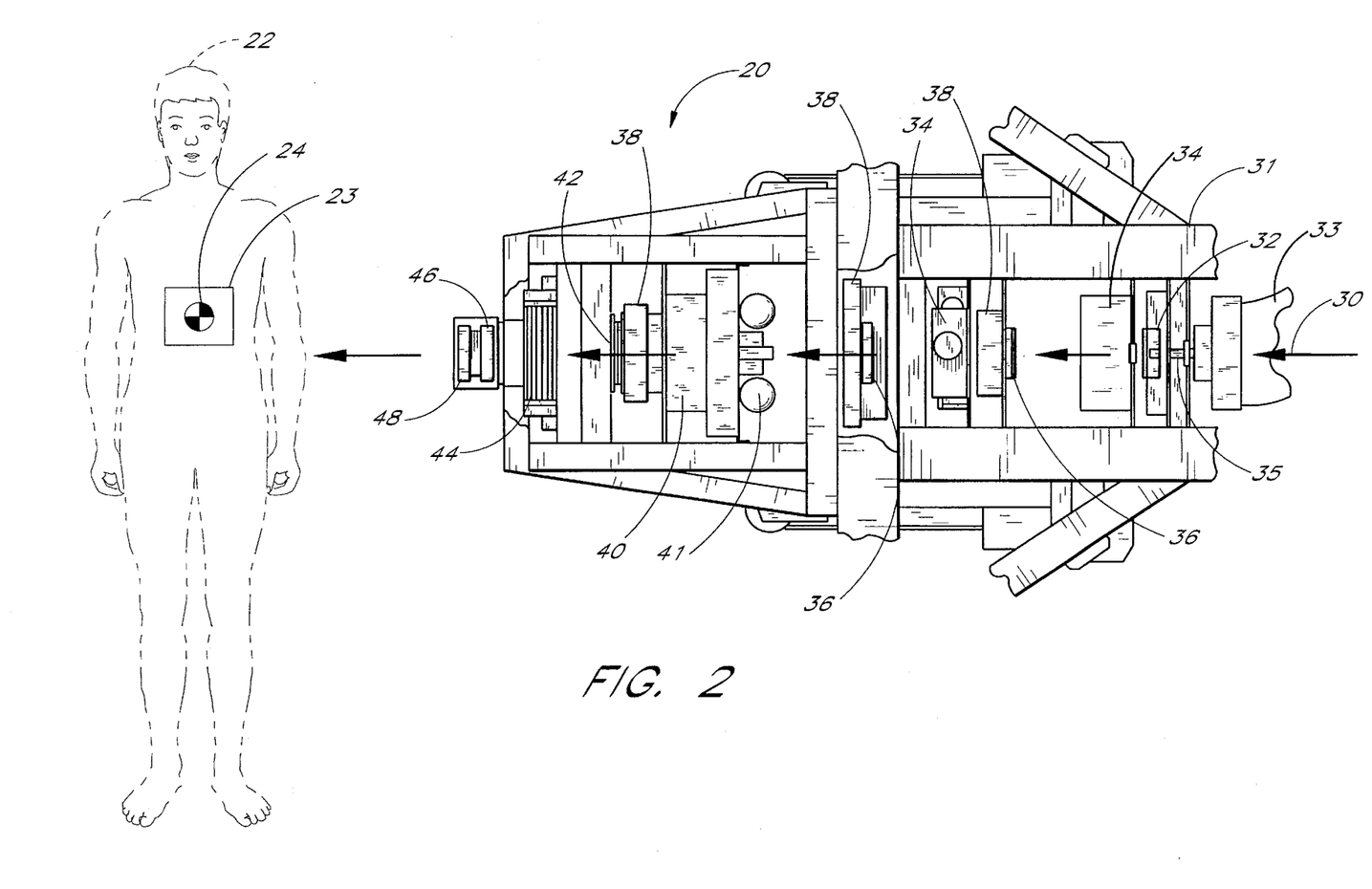
FIG. 2 is a partial plan view of an exemplary proton beam delivery system.

Important elements of a radiation treatment plan are established by the component configuration of beam delivery systems, such as that shown in FIG. 2. A primary consideration in any treatment plan is the proton beam energy, determined by the energy of the incoming beam 30 and subsequent beam scatterers 34. Another element of the patient treatment is the field size determined by fixed apertures 38 and preferably a patient specific aperture 46. The depth of penetration is influenced by an energy dispersive element or range modulator 40, while beam profile and contour are controlled by the size and shape of bolus 48. The entire delivery system 20 is rotated about beam isocenter 24 in order to obtain a plurality of beam trajectories within the patient 22.

The delivery system 20 has detectors which are located along beam path of the delivery system, which monitor the aforementioned beam configuration operations. For example, the SEM 32 is primarily suited to measure total beam fluence over a wide range of beam parameters. Two so-called Proton Transmission Ion Chambers (PTIC) 36 are comprised of five channels, measuring beam fluence as well as beam position. A Multi-Element Transmission Ion Chamber (METIC) 42 comprises a spatial array of 320 detector channels allowing beam profile, position and fluence to be monitored. The delivery system detectors are calibrated with the help of a calibrated detector 23, shown schematically as a box positioned at the isocenter 24 in place of the patient 22. The calibrated detector is temporarily placed at beam isocenter 22 during a beam calibration operation described below.

Figure 3:
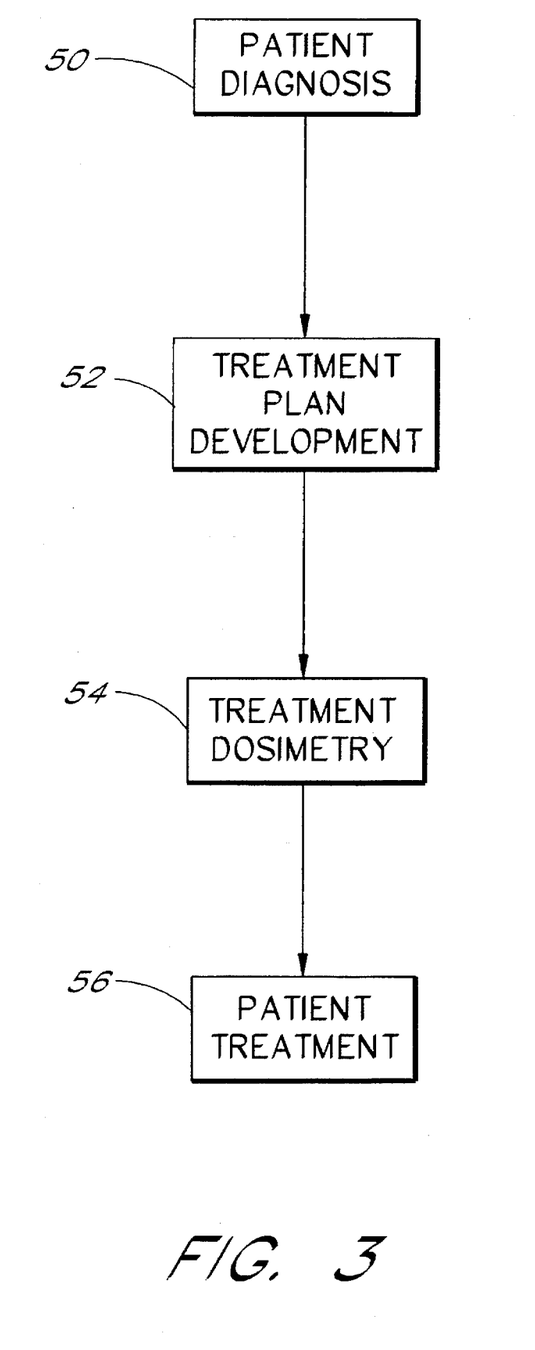
FIG. 3 is a block diagram showing the basic process elements leading to proton beam therapy.

The process of treating a patient with proton radiation entails several preliminary steps as shown schematically in FIG. 3. Initially, a patient diagnosis is developed to specify the nature and extent of afflicted tissue, for example in terms of tissue condition, location, volume, and shape. Such a diagnosis is indicated by process block 50. An appropriate online prescription or treatment plan is developed in response to the diagnosis as indicated by process block 52. The treatment plan typically specifies the relevant beam parameters which provide the most effective radiation treatment. For example, elements of the treatment plan may specify beam energy, position and angle of the delivery system 20 with respect to the patient 22 as well as delivery system elements such as aperture 46, bolus 48, range modulator 40 and scatterers 34. In general, the delivered dose changes with many treatment plan parameters, such as beam location and angle of entry into the patient 22, specific size and shape of the bolus 48, size of the aperture 46 and specifications of the range modulator 40. For accurate dose determination, it is therefore necessary to determine detector calibration functions $f_p^i$ corresponding to a particular treatment plan, where the subscript i is indexed to a specific delivery system detector channel. Proper dosimetric conditions are established by the treatment plan dosimetry, which process calibrates the detector channels $d^i$ comprising delivery system detectors 32, 36 and 42 under the conditions of the specified treatment plan 52; in effect a trial patient treatment, indicated in FIG. 3 by process block 54. The treatment of the patient 22 is indicated by process block 56, and is administered once treatment dosimetry is established.

Treatment plan dosimetry is performed by supplying a metered radiation exposure to a phantom or semi-realistic target containing a calibrated detector 23 illustrated schematically in FIG. 2. The detector 23, preferably a calibrated detector traceable to the National Institute of Standards and Technology, measures the absolute deposited radiation dose during the metered period of radiation exposure. Preferably the treatment dosimetry comprises radiation delivery to the phantom target 23 positioned at the isocenter 24, under the conditions specified by treatment plan. A phantom may for example comprise a suitable volume of water, having an influence on the incident radiation beam closely approximating that of the intervening tissue, within which is disposed a calibrated position sensitive charged particle detector. Calibration functions $f_p^i$ are generated for the detector channels i of delivery system detectors 32, 36 and 42 under the conditions of the treatment plan. The calibration functions $f_p^i$ are functions of the detector channel signals $d_i$ and relate the detected quantity $d^i$, such as charge or current, to a corresponding quantity of delivered radiation $D_p$, calibrated in Grays, such that $D_p=f_p^i(d^i)$. Preferably the delivery system components and detectors respond in a linear manner to changes in incident beam flux, in which case it is advantageous to specify a multiplicative calibration factor $C_p^i$ such that $D_p=C_p^i*d^i$ (i.e. $f_p^i=C_p^i$) for each detector channel $d^i$ taken separately. In the present preferred embodiments, it is assumed that the calibration functions $f_p^i$ are linear functions of the detector channel rates $d^i$; however it will be appreciated that the methods and apparatus of the present embodiments may also encompass non-linear calibration functions as well. Specifically, for a given beam fluence and delivery system configuration corresponding to a particular patient treatment plan, the administered dose $D_p$ is proportional to the time period of radiation exposure $\Delta t_p$. Thus, under the specific conditions corresponding to treatment plan, it is sufficient to characterize the delivered dose $D_p$ by the calibration factor $C_p^i$ as long as the beam fluence remains constant. The aforementioned treatment dosimetry is represented in FIG. 3 by the process block 54, after which patient treatment using the calibrated delivery system may follow, indicated by process block 56.

While it may be sufficient to monitor the administered dose with a single calibrated delivery system fluence detector; the accuracy and precision of delivery system 20 is greatly enhanced through redundancy and correlation by calibrating the plurality of detector channels $d_i$ in a delivery system 20. Treatment plan dosimetry preferably generates an array of calibration functions $f_p^i$ or factors $C_p^i$ related by their relative fluence $d^i$ under a given beam configuration, where again i is indexed to a specific detector channel. Accordingly, a delivered dose $D_p$ during treatment is determined by a plurality of calibrated detectors $D_p=C_p^i*d^i$, wherein the accuracy of each may be weighted by their relative beam flux. Redundant detector elements provide a greater degree of accuracy, precision and consistency in proton therapy dosimetry. Furthermore, the ensemble of calibrated delivery system detectors provides useful cross-correlated information for monitoring the full range of proton beam properties, such as position, size and profile. In the event of beam drift or configuration changes, detector correlation provides a high degree of security from misexposure.

As described earlier, the process of treatment plan calibration consumes much of the operating time and cost of an expensive proton beam therapy facility. Treatment cost, efficiency, flexibility and turn-around time could be dramatically improved upon reduction or elimination of this phase of operation. To address this issue, a basic form of a preferred method for delivery system calibration utilizes a treatment plan database 66, comprised of previously calibrated treatment plans, to correlate a specific treatment plan to the corresponding appropriate detector calibration factors $C_p^i$. As illustrated in the flow diagram of FIG. 4, a patient is first diagnosed and then a treatment plan established as represented by process blocks 50 and 52 respectively. Process block 58 represents a comparison between the current treatment plan and previously generated and calibrated treatment plans stored in treatment database 66. A decision block 60 determines if there is a suitable match between the current treatment plan 52 and a previously calibrated treatment plan in database 66, according to predetermined dosimetric tolerances. If a match is found, then delivery system calibration factors $C_p^i$ are derived from those of the matching treatment plan as indicated in process block 62. In the event no match is found, treatment plan dosimetry, indicated by the process block 54, is performed to determine new calibration functions $C_p^i$ corresponding to the current treatment plan. These new data are incorporated into the treatment database 66 for future comparisons as indicated by process block 64. Subsequent patient treatment, indicated by process block 56, is performed using either the stored or measured calibration factors, as determined by decision block 60.

Figure 4:
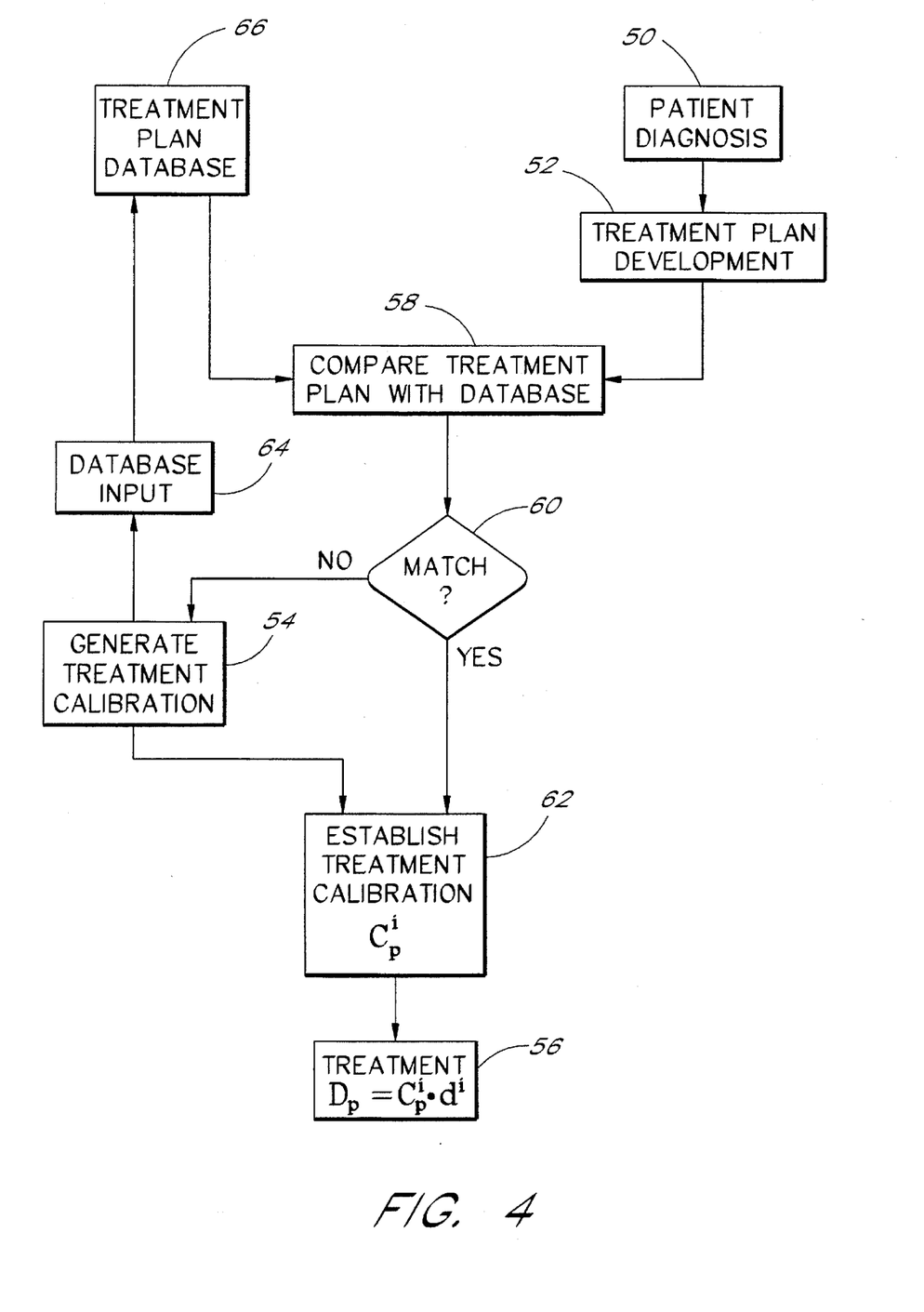
FIG. 4 is a flow diagram of the basic form of a preferred method of delivery system calibration.

The comparison indicated by process block 58 comprises determining a correspondence between a current online prescription to that contained in the treatment database 66. In general such a comparison is based upon the plurality of elements comprising the treatment plan 52. For example, proton beam energy, field size and range is compared to determine the existence of a suitable match. The criterion for a suitable match indicated in process block 60 may require that corresponding discrete parameters such as beam energy, scatterers, and range modulating devices match identically. Furthermore, continuous parameters specified in the treatment plan such as position and angle of beam entry may be specified to agree with an existing treatment plan within a predetermined tolerance established by clinical testing. Still other parameters may be compared to a statistical treatment of database entries. For example, database entries may be treated by a discrete moving average, in which field size is locally sampled and averaged. Patient calibration factors for the current treatment plan may be estimated by an interpolation between these discretely averaged loci of database points.

Practical delivery systems, such as that shown in FIG. 2, commonly entail multiple beam operations and a plurality of beam monitors; the complex relationship between treatment plan parameters and detector calibration factors render accurate dose prediction very difficult. On the other hand, the present method of delivery system calibration described here obviates the need for a separate treatment plan dosimetry for every treated patient, representing a significant improvement in operation efficiency. In this basic embodiment of the preferred method, treatment database 66 comprises a look-up table, in effect wherein the transfer function of the delivery system is tabulated. As new treatments are incorporated, the probability of a suitable match increases, thus, the efficiency of this calibration method increases with the number of patients served. In practical terms, a calibration database may approach completion on a proportional basis with a time constant of about 1 year.

The essential feasibility of treatment database 66 is predicated on certain basic conditions observed to exist in a preferred proton beam therapy facility 10, namely long term operation stability and stability under system or component exchange. In practice, long term drift in beam delivery system 20 operation is well below the accepted tolerance of about 2.5% for dosimetric accuracy. The dose-to-dose performance of a proton beam configuration using nominally equivalent delivery systems 20 and delivery system components such as scatterers 34, apertures 46 and boluses 48 is also within dose delivery tolerance. Thus, in spite of the rather complicated operations performed on the proton beam during delivery, their relationship to detector calibration factors $C_p^i$ remains substantially unaltered. These circumstances have important implications for operation efficiency of a clinically-based, multiple delivery proton beam treatment center 10, and in particular for the following preferred method of normalizing delivery system 20.

The influence of even small variations in delivery system behavior could render new treatment dosimetry necessary over time, system or component exchange. However, the method of delivery system normalization according to the present invention comprises a standard detector calibration using a standard fixed set of beam configuration parameters, including a standard dose delivery $D_n$. The standard calibration or baseline dosimetry generates a set of normalizing factors $N_j^i$ for detector channels $d_j^i$, such that $D_n = N_j^i * d_j^i$, where now i refers to the corresponding detector channels of delivery system j. The normalizing factors $N_j^i$ provide a reference for the treatment plan calibration factors $C_{pj}^i$ in the event of changes or deviations in delivery system or detector response. Specifically, a repeated baseline dosimetry generates a new set of normalizing factors $N_k^{i''}$ reflecting any small changes in the system response with respect to the previous normalization and normalizing factors $N_j^i$. The treatment calibration factors $C_{pj}^i$, specific to a delivery system j, are modified in response to changes in delivery system behavior as detected by the repeated normalization procedure as follows: $C_{pk}^{i''} = \{N_k^{i''}/N_j^i\} * C_{pj}^i$. Accordingly, patient treatment plan is administered using the normalized treatment plan calibration factors $C_{pk}^{i''}$.

Figure 5:
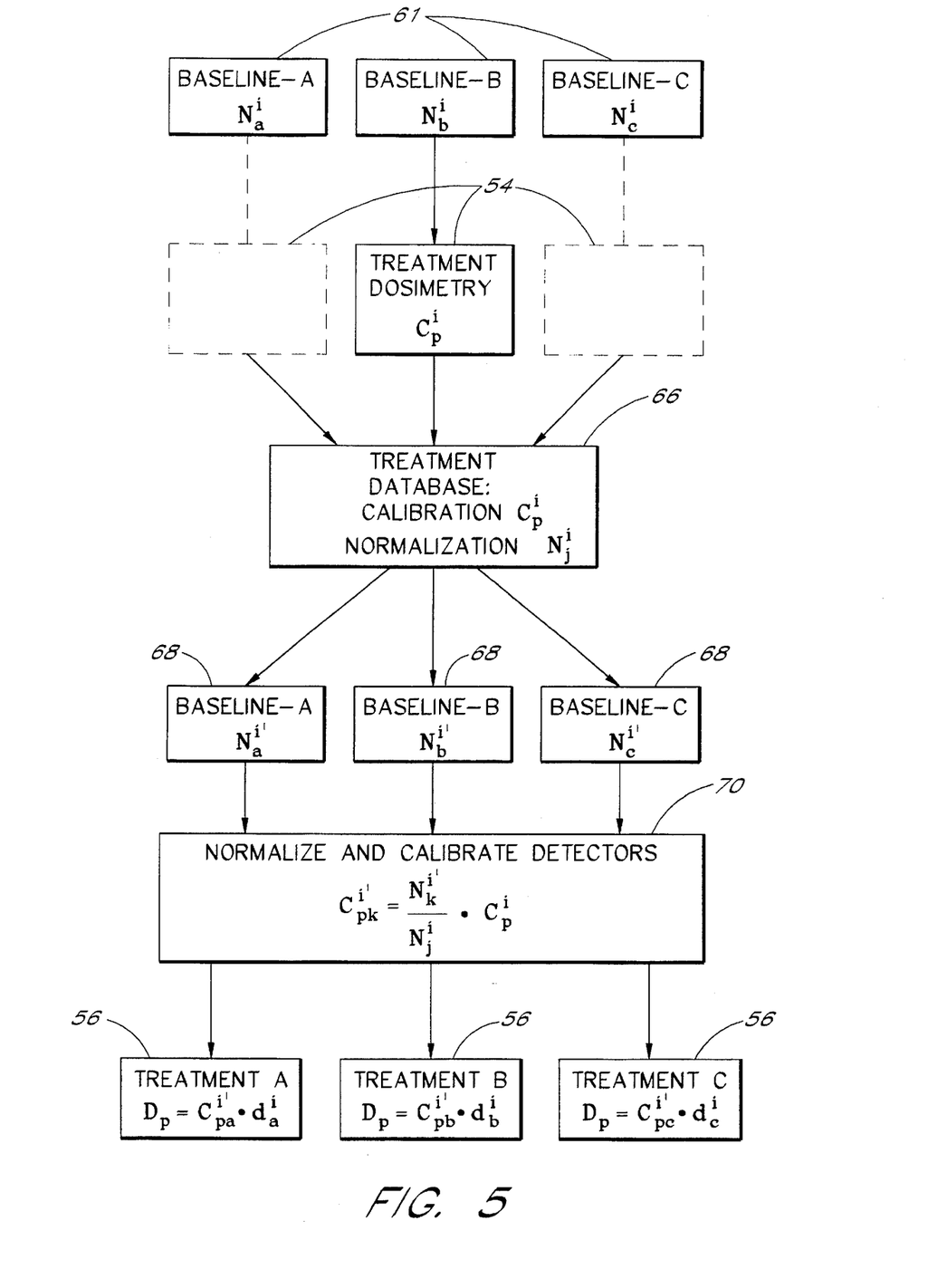
FIG. 5 is a block diagram outlining elements of the preferred method of the present invention.

As illustrated in the block diagram of FIG. 5, a baseline dosimetry, indicated by process block 61, conducted near the time of treatment using a standard delivery system configuration, generates a set of reference normalizing factors $N_j^i$ associated and stored with treatment plan calibration factors $C_{pj}^i$ in the treatment database 66. The baseline calibration is performed for every nominally equivalent treatment delivery system j, preferably on a daily basis. Accordingly, an array of normalization factors is generated and stored in database 66 along with calibration factors $C_{pj}^i$, which span the range of detector channels $d^{ji}$, delivery systems j and time. Under independent, but nominally equivalent conditions, for example at a different time or delivery system, a substantially identical baseline dosimetry, indicated by process block 68, is repeated to generate an independent set of reference normalizing factors $N_k^{i''}$. These new reference normalizing factors $N_k^{i''}$ presumably reflect any small changes in the system with respect to the previous standard baseline normalization and normalizing factors $N_j^i$ corresponding to treatment calibration factors $C_{pj}^i$. Based on these sets of normalizing factors, treatment plan calibration factors $C_{pj}^i$ are modified to remain accurate in the presence of the aforementioned variations such that $C_{pk}^{i''} = \{N_k^{i''}/N_j^i\} * C_{pj}^i$, as indicated in block 70. Accordingly, patient treatment, shown in process block 56, is carried out using the normalized treatment plan calibration factors $C_{pk}^{i''}$.

Since other equivalent delivery systems are normalized in the same manner, the patient treatment may be carried out at another of the normalized delivery systems, shown here by a plurality of patient treatment process blocks 56. For example, as indicated by the solid box 54 in FIG. 5, calibration factors $C_{pb}^i$ initially derived in delivery system B, are adjusted at box 70 for application at any of delivery systems A, B or C. Hence, while the original treatment was calibrated and carried out using a specific delivery system, other equivalent delivery systems may be normalized to provide the same dosimetric accuracy. These considerations also hold for changes within a particular delivery system; for example, in the event of drift over time or component exchange, the delivery system performance may be normalized to provide the same dosimetric accuracy. Thus, patient treatment may be administered at any available nominally equivalent delivery system.

The delivery system normalization herein disclosed is not limited to delivery systems or detectors therein displaying linear response characteristics. Similar to the calibration procedure and calibrating functions $f_p^i$ described earlier, normalizing factors $N_j^i$ may be extended to include non-linear system response by use of normalizing functions $f_{nj}^i$ of detector channels $d_j^i$, such that $D_n = f_{nj}^i(d_j^i)$, where again $D_n$ is a dose delivery under standard beam conditions. The previously determined calibration functions $f_p^i$ are modified by the normalizing functions $f_{nj}^i$, $fnk^{i_i}$ to reflect changes in system response. The specific manner in which the calibration functions $f_p^i$ are modified by the normalizing functions $f_{nj}^i$, $f_{nk}^{i_i}$ will depend on the respective functional forms; however, in general the calibration functions $f_p^i$ may be considered functionals of the normalizing functions $f_{nj}^i$, $f_{nk}^{i_i}$ such that $f_{pk}^{i_i} = f_{pj}^i [f_{nk}^{i_i}, f_{nj}^i, d_k^i]$, thus correcting the calibration functions $f_{pj}^i$ for a wide range of delivery system response.

Moreover, just as the calibration functions $f_{pj}^i$ are defined and determined under a specific set of beam conditions, so too are the normalizing functions $f_{nj}^i$ which relate the detector channel readings $d_j^i$ to a corresponding delivered dose $D_n$ under a standard set of operating conditions and exposure time. Accordingly, even when the delivery system and detectors display non-linear response, the normalizing functions are preferably approximated by normalizing factor $N_j^i$ for a given specific range of operating conditions. It would be appreciated that for such relationships to hold, the overall transfer function of the delivery system is preferably continuous, and the observed deviations to be normalized are preferably small with respect existing non-linearities in the transfer function. In practice, such deviations are observed to lie within the dose delivery tolerance of about 2.5%.

Figure 6:
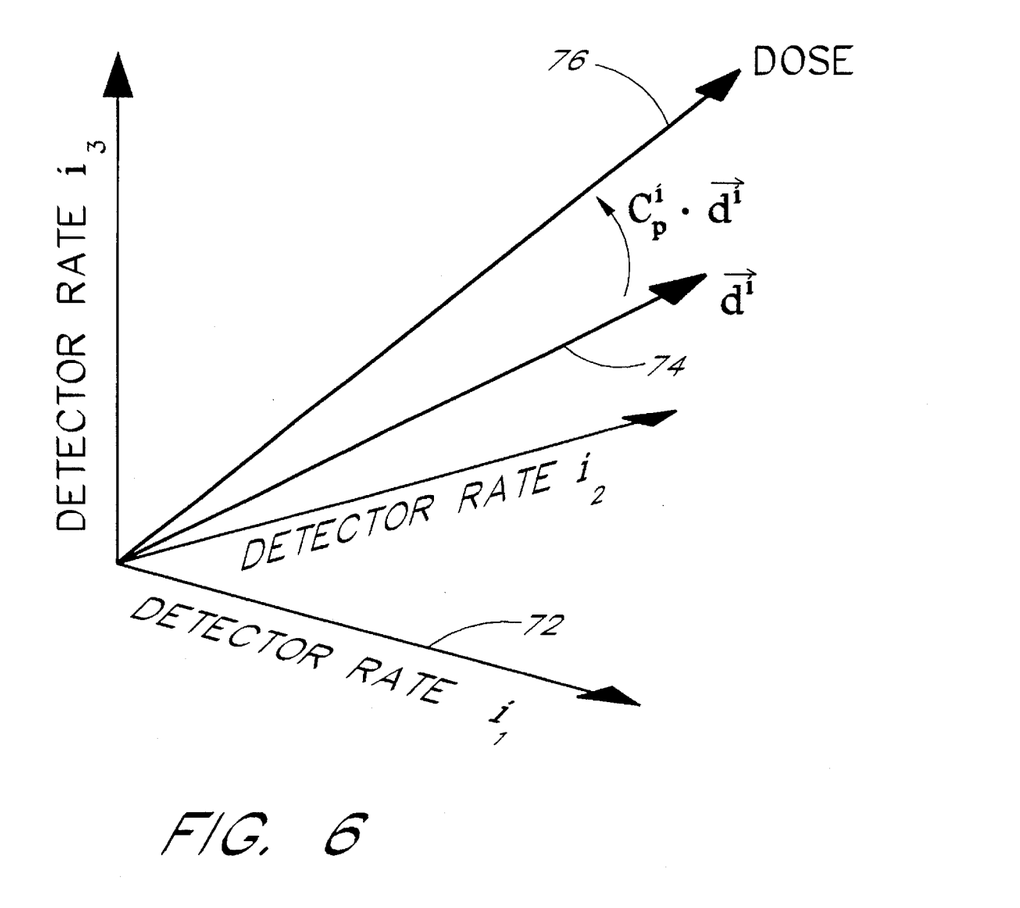
FIG. 6 is a vector representation of detector configuration and delivery system normalization.

The vector representation of FIG. 6 illustrates the general behavior of the preferred embodiment for normalization and calibration. For a given treatment plan the array of observed detector rates $dp_i$ may be represented as a vector 74 in an $i^{th}$ dimensional coordinate representation, wherein each axis represents an individual detector channel rate 72 in a given delivery system. The calibration and normalization factors $C_p^i$ and $N^i$ are represented by transformations of detector vector 74 onto the unit dose vector 76, whose i components are equal in length and correspond to the treatment dose $D_p$. The preferred factors herein described and whose transformations are depicted in FIG. 6, treat detector channels $d^i$ independently; accordingly the calibration factor or transformation coefficient for each detector channel is $D_p/d^i$. Furthermore, the preferred response is linear for each detector channel $d^i$ in the delivery system 20, and consequently, normalization functions between nominally equivalent but distinct delivery systems 20 or components thereof is linear in the corresponding detector channels $d^i$.

Figure 7:
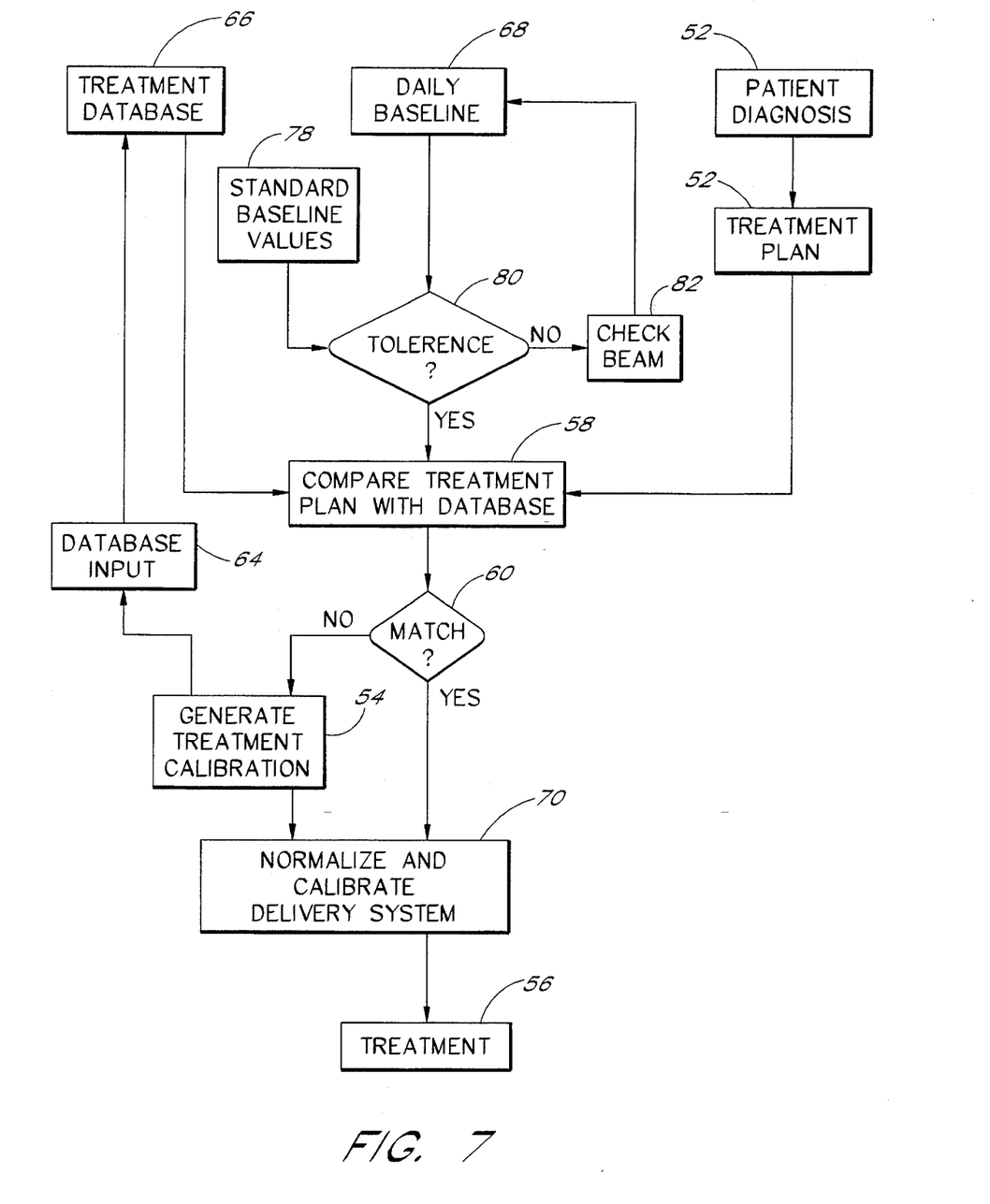
FIG. 7 is a flow diagram of the preferred form of the method of the present invention.

In a preferred embodiment for delivery system normalization and calibration, a comprehensive database containing previously calibrated treatment plans, corresponding calibration factors and baseline normalization factors provides for multiple delivery system therapy using the original treatment plan calibration factors. Thus, the preferred embodiment herein disclosed minimizes the frequency of performing the lengthy and expensive treatment plan calibration. As shown in the flow diagram of FIG. 7, a preferred method of normalizing and calibrating delivery system 20 begins with the daily baseline normalization, indicated by the process block 68, carried out under a standard set of operating conditions, shown in block 78. The decision block 80 is executed to determine if baseline normalization factors 68 are out of tolerance with standard values 78. If tolerance is not met, then beamline components are checked, in process block 82. If tolerance is met, then a current treatment plan, in block 52, is compared to the treatment plan database 66 shown at process block 58. An appropriate match is determined through decision block 60, whereupon delivery system detectors are normalized and calibrated 70 according to the treatment plan calibration factors and baseline normalization factors. Patient treatment, in block 56, follows with dosimetry by the normalized and calibrated delivery system detectors. If no suitable match is found in decision block 60, then treatment plan dosimetry, in block 54, provides the necessary information for patient treatment, at block 56, as well as new database information 64.

The method of delivery system normalization and calibration herein disclosed is quite general, applying broadly to a set of substantially equivalent proton beam delivery systems whose transfer characteristics may be determined to a desired level of accuracy. The practical consequences for a clinically-based proton beam therapy facility 10 are particularly important. Treatment may be administered at different times and with different delivery systems 20 without repeating treatment plan calibration. The method described here therefore satisfies an important requirement for clinical proton beam delivery systems and represents a significant step in efficiency and cost reduction.

Numerous variations and modifications can be envisioned without departing from the spirit of the present invention. Therefore, it should be understood that the forms of the present invention described above and shown in the accompanying figures are illustrative only and are not intended to limit the scope of the present invention. Accordingly, the scope of the present invention is to be ascertained with reference to the claims.

We claim:

1. A method of treating a patient with proton radiation, comprising:
    (a) utilizing a first beam delivery system to emit a proton radiation beam having a standard beam configuration;
    (b) detecting the radiation dose supplied by the beam of standard configuration;
    (c) utilizing said first beam delivery system to emit a proton radiation beam having a beam configuration tailored for a specific treatment plan;
    (d) detecting the radiation supplied by the beam configured for the specific treatment plan and producing a signal corresponding to the detected radiation;
    (e) comparing the signal detected in step (d) with calibrated dose detection data to develop at least one treatment plan calibration factor;
    (f) treating said patient with a proton radiation beam that has been calibrated with said treatment plan calibration factor and that is configured for the specific treatment plan;
    (g) subsequent to steps (a)–(f), utilizing a second beam delivery system to emit another proton radiation beam having said standard beam configuration;
    (h) detecting the radiation dose supplied by the subsequent proton radiation beam having the standard beam configuration;
    (i) comparing the dose detected in step (h) with the dose detected in step (b) to develop at least one normalizing factor;
    (j) utilizing said second beam delivery system to emit a normalized proton radiation beam tailored for said specific treatment plan by utilizing said normalizing factor; and
    (k) treating said patient with the normalized proton radiation beam configured for said specific treatment plan.

2. The method of claim 1, wherein said first beam delivery system comprises a first nozzle mounted on a first gantry and said second beam delivery system comprises a second nozzle mounted on a second gantry.

3. The method of claim 2, wherein the first beam delivery system used to perform steps (a) and (c) has a structural configuration which is substantially the same as the second beam delivery system used to perform steps (g) and (j).

4. The method of claim 1, further comprising the steps of compiling a database containing a plurality of previously calibrated proton radiation beam treatment plans and the corresponding normalizing and calibration factors.

5. The method of claim 4, comprising the steps of comparing a prescribed proton radiation beam treatment plan to the previously calibrated proton radiation beam treatment plan to derive normalizing and calibrating factors for the prescribed plan.

6. The method of claim 1, wherein the steps (a), (c), and (j) comprise receiving the proton radiation beam and directing the radiation to a target position for depositing the proton radiation.

7. The method of claim 6, wherein step (d) comprise:

measuring the signal of a first radiation detector disposed along the proton beam path and having a signal output that is a function of the incident proton radiation dose; and wherein step (e) comprises:

measuring the signal of a second radiation detector disposed at said target position and having an output signal that is calibrated to measure the received radiation dose; and comparing the signals of said first and second radiation detectors to derive said treatment plan calibration factor.

* * * * *